(12) United States Patent
Wanderer

(10) Patent No.: US 8,389,474 B1
(45) Date of Patent: Mar. 5, 2013

(54) RATIONALE FOR IL-1 β TARGETED THERAPY TO IMPROVE HARVESTED ORGAN VIABILITY, ALLOGRAFT TOLERANCE, REPLANT SUCCESS AND FOR CONDITIONS CHARACTERIZED BY REDUCED OR ABSENT ARTERIAL PERFUSION

(76) Inventor: Alan Anson Wanderer, Bozeman, MT (US)

( * ) Notice: Subject to any disclaimer, the term of this patent is extended or adjusted under 35 U.S.C. 154(b) by 82 days.

(21) Appl. No.: 12/803,920

(22) Filed: Jul. 9, 2010

Related U.S. Application Data

(60) Provisional application No. 61/270,834, filed on Jul. 14, 2009.

(51) Int. Cl.
*A61K 38/00* (2006.01)
*A61K 39/00* (2006.01)

(52) U.S. Cl. .................. 514/12.2; 424/141.1; 424/145.1

(58) Field of Classification Search .................. None
See application file for complete search history.

(56) References Cited

U.S. PATENT DOCUMENTS

| | | | | |
|---|---|---|---|---|
| 5,800,815 | A * | 9/1998 | Chestnut et al. | 424/153.1 |
| 5,869,519 | A * | 2/1999 | Karanewsky et al. | 514/415 |
| 6,656,462 | B2 * | 12/2003 | Dondero et al. | 424/85.2 |
| 6,670,321 | B1 * | 12/2003 | Adamis | 424/134.1 |
| 6,878,743 | B2 * | 4/2005 | Choong et al. | 514/448 |
| 7,220,538 | B2 * | 5/2007 | Fischer et al. | 435/1.1 |
| 2001/0053764 | A1 * | 12/2001 | Sims et al. | 514/12 |
| 2008/0044414 | A1 * | 2/2008 | Masat et al. | 424/136.1 |
| 2010/0121273 | A1 * | 5/2010 | Kochanek et al. | 604/113 |

FOREIGN PATENT DOCUMENTS

| EP | 1 208 748 A1 * | 5/2002 |
|---|---|---|
| WO | WO 02/16436 A2 * | 2/2002 |
| WO | WO 02/094263 A2 * | 11/2002 |
| WO | WO 2007/064846 A2 * | 6/2007 |

OTHER PUBLICATIONS

Mathiak et al., 2000, British Journal of Pharmacology 131:383-386.*
Schierle et al., 1999, Nature Medicine 5:97-100.*

* cited by examiner

*Primary Examiner* — Elizabeth C Kemmerer

(57) ABSTRACT

Ischemia-reperfusion (IR) injury involving harvested organs and allograft transplantation may be increased by stimulation of a newly described innate pro-inflammatory immune system (i.e.NALP-3-inflammasome) which can cause secretion of IL-1β and subsequent neutrophilic inflammation. Ischemia and hypoxia can cause metabolic acidosis and development of danger signals known to stimulate IL-1β secretion from the NALP-3 inflammasome. Based on this newly discovered mechanism causing pathobiology in IRI, IL-1β targeted therapy would be capable of improving allograft tolerance, viability of harvested organs and in conditions with compromised arterial blood supply and subsequent reperfusion, such as replants, compartment syndrome, and serious vascular accidents.

10 Claims, 1 Drawing Sheet

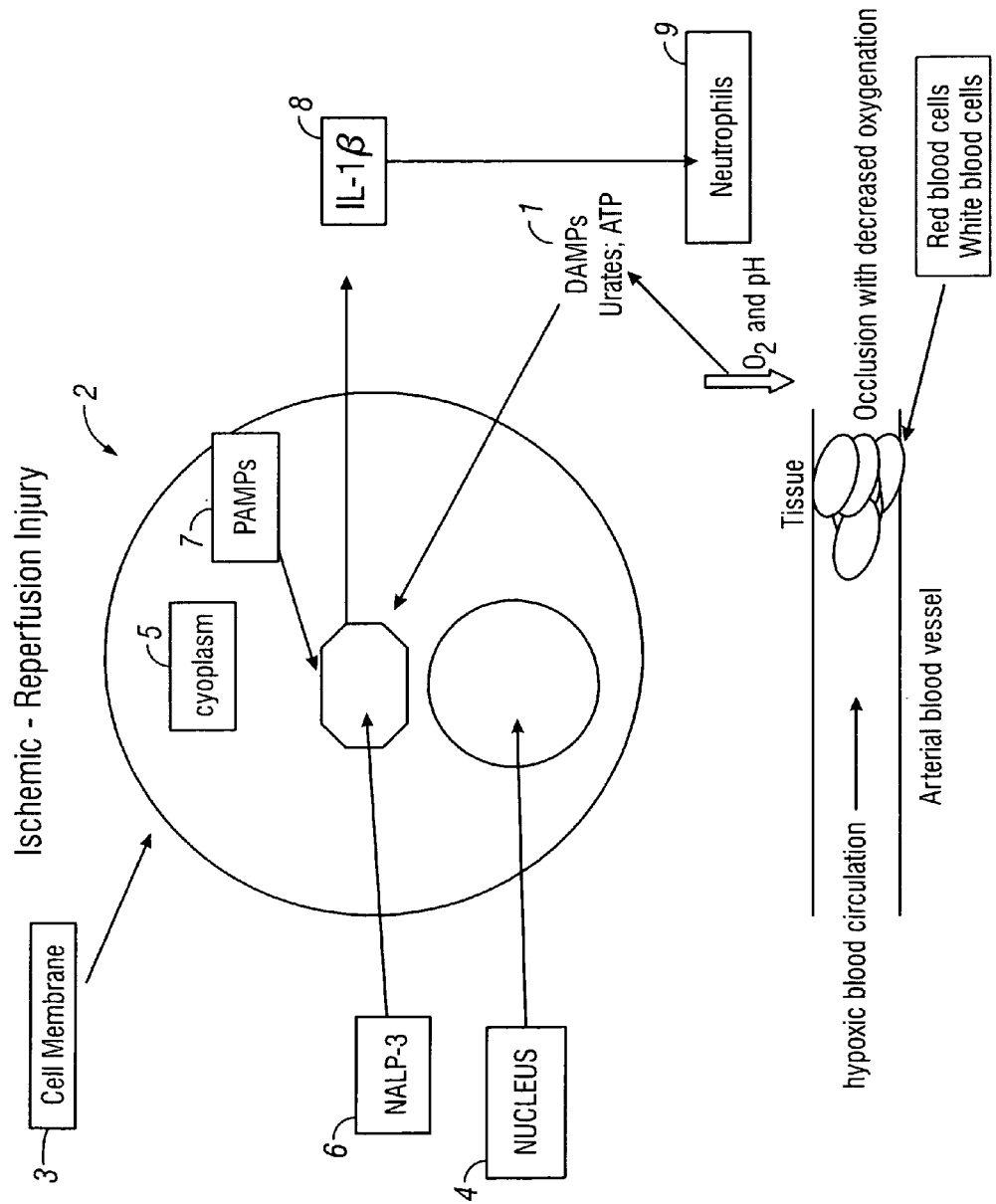

RATIONALE FOR IL-1 β TARGETED THERAPY TO IMPROVE HARVESTED ORGAN VIABILITY, ALLOGRAFT TOLERANCE, REPLANT SUCCESS AND FOR CONDITIONS CHARACTERIZED BY REDUCED OR ABSENT ARTERIAL PERFUSION

This non-provisional U.S. Patent application claims the benefit of Provisional Application: U.S. Application No. 61/270,834 filed on Jul. 14, 2009, confirmation No. 7872

BACKGROUND OF THE INVENTION

Ischemia-reperfusion injury (IRI) involving harvested organs and allograft transplantation may in part be caused by stimulation of a newly described innate pro-inflammatory immune system (i.e. cryopyrin-inflammasome, now referred to as NLRP-3 or NALP-3 inflammasome) that is known to cause secretion of pro-inflammatory cytokines (IL-1β) and induction of robust neutrophilic inflammation. Several biochemical triggers can stimulate the NALP-3 inflammasome and are referred to as danger associated molecular patterns (DAMPs), such as extracellular ATP, uric acid/urate (UA)/ calcium pyrophosphate (CaPP) crystals, hyaluronan and intracellular hypokalemia. It is likely DAMPs are formed during IRI associated with transplantation pathobiology, as ischemia can induce anaerobic metabolism with metabolic acidosis from a combination of lactic acidosis, release of hydrogen ions during catabolism of ATP and accumulation of carbon dioxide. Reperfusion causes increased oxidants that can also lead to DAMPs formation and subsequent neutrophilic inflammation. Reduced pH disrupts mitochondrial ATP production, creating alterations in ion channels and membrane dissolution, resulting in intracellular sodium and calcium ion influx with potassium ion efflux and subsequent intracellular hypokalemia. Extracellular ATP can also stimulate purinergic P2X membrane receptors and cause further efflux of potassium ions from cells. Purine catabolism of nucleic acids and ATP in stressed and dying cells is associated with increased concentrations of UA that can crystallize at lower pH. ATP utilization during anaerobic metabolism leads to formation of pyrophosphates, which can combine with calcium ions to form CaPP. Moreover, released ATP from cytotoxic injury can bind to cryopyrin (i.e. putative protein of NALP-3 inflammasome) which has ATPase activity and can cause further increased production of UA and pyrophosphates. Consequently, these biochemical events circumstantially support the likelihood that IR transplantation pathobiology can induce DAMPs.

The NALP-3 inflammasome is located in the cytoplasm of various cell types (monocytes, neutrophils, mast cells, dendritic cells, macrophages, glia and chondrocytes) and following DAMPs stimulation, can activate caspase-1 to catalyze stored pro-IL-1β to IL-1β, with subsequent secretion of IL-1β. This pro-inflammatory cytokine in turn can provoke a cascade of pro-inflammatory events (i.e. up-regulation of vascular adhesion molecules (ICAM), IL-6 release, increased neutrophil and monocyte chemokines, IL-17 A secretion), that can induce marked neutrophilic inflammation in IRI. Since a central part of transplantation pathobiology is associated with IRI, it is posited that secretion of IL-1β by DAMPs stimulation of NALP-3 inflammasomes may play a significant role in causing neutrophilic inflammation and thereby reduce viability of harvested organs and increase allograft rejection.

Research involving rare autosomal dominant auto-inflammatory disorders led to the original discovery of the NALP-3 inflammasome. Hoffman et. al first identified the cryopyrin-encoding gene on chromosome 1q44 by investigating Familial Cold Auto-Inflammatory Syndrome (FCAS), a rare autosomal dominant syndrome characterized by cold exposure induction of IL-1β secretion that causes fever, neutrophilic leukocytosis, acute phase reactant elevations, and neutrophil leukocyte infiltrated dermatosis. The cryopyrin gene discovery led to recognition of the NALP-3 inflammasome by Martinon et al, a cytoplasmic macromolecular protein complex containing the putative protein cryopyrin and other adaptor proteins. Two other rare and seemingly unrelated autosomal dominant periodic fever syndromes (i.e. Muckle-Wells and Neonatal Onset Multisystem Inflammatory Disease, i.e. NOMID) with dysregulated elevated 1 L-1β production and profound neutrophilic inflammation were found to have mutations on the same gene. All three auto-inflammatory hereditary syndromes, referred to as cryopyrin-associated periodic syndromes (CAPS), are exceptionally responsive to IL-1β targeted therapy (IL-1β TT), which provided unequivocal evidence for IL-1β mediation of robust neutrophilic inflammation in human disorders. There is further evidence to suggest that blocking IL-1β can not only diminish neutrophilic inflammation in CAPS but also in several other IL-1β mediated neutrophilic inflammatory disorders, such as recalcitrant gout, Still's juvenile arthritis and Schnitzler's syndrome. More recently, autosomal recessive syndromes with deficiency of naturally occurring IL-1β receptor antagonists have been described. These syndromes exhibit manifestations of unopposed IL-1β mediated neutrophilia with pustulosis and osteomyelitis, which are also very responsive to IL-1β targeted therapy (IL-1β TT). The excellent response to IL-1βTT in the aforementioned conditions provides the rationale for its consideration in treating IRI transplantation pathobiology characterized by IL-1β secretion and dominant neutrophilic inflammation, as observed in many animal and human IR models following de-oxygenation stress.

It is known that IL-1β secretion can occur following pathogen associated molecular pattern (PAMPs) stimulation of innate immune receptors, such as cytoplasmic receptors (i.e. NALP-3 inflammasome, NALP-1 inflammasome, and IPAF inflammasome) and membrane associated receptors referred to as toll-like receptors (TLRs'). It is likely that PAMPs stimulation of innate immune receptors explain some IL-1β secretion and neutrophilic inflammation in infectious diseases, such as post-operative infectious disease complications following organ transplantations. However in contrast, many healthy animal models of IRI (i.e. cerebral, renal, intestinal and an ex-vivo human cardiac model), with no evidence of detectable PAMPs have demonstrated secretion of IL-1β within one hour of de-oxygenation after arterial blood vessel occlusion or during ex-vivo cardiac tissue perfusion with buffered fluids. Subsequent development of prominent neutrophilic inflammation was consistently observed in the arterial blood vessel occlusion studies and in several of these models, IL-1β targeted therapy (IL-1β TT) reduced the extent of the neutrophilic inflammation and injury. Until recently, there has been no reasonable explanation for induction of IL-1β secretion and neutrophilic inflammation following de-oxygenation in IR models, absent detectable PAMPs. Although PAMPs could have been present in undetectable concentrations in these animal experiments, it remains unclear why low concentrations of PAMPs would stimulate IL-1β secretion and cause neutrophilic inflammation only after arterial occlusion. Giamarellos-Bourboulis et al provided an interesting observation as monocytes challenged by urates in combination with LPS caused synergistic secretion of IL-1β, suggesting that even low and possibly undetectable concentrations of PAMPs may require DAMPs to induce IL-1β secretion in certain circumstances, such as following arterial occlusion.

BRIEF SUMMARY OF THE INVENTION

In summary, the novelty of this patent is providing a new paradigm connecting transplantation outcomes to knowledge gained from the recognition of the NALP-3 inflammasome which can be stimulated by DAMPs formation during IR injury and no subsequent stimulation of the NALP-3 inflammasome, followed by caspase-1 activation, IL-1β secretion, and ischemic induced necrosis defined by neutrophilic inflammation and allograft rejection.

The second object is recognition that based on the aforementioned mechanism, there is rationale for use of IL-1β TT to reduce neutrophilic inflammation that occurs during IRI with harvested organs and in transplanted organs affected by ischemia and reperfusion intervention. It is noteworthy that there have been no medical reports of any past or concurrent trials with IL-1β TT prior to the filing date on which this patent depends. There is also evidence that explanted organs can exhibit an inflammatory cytokine burst immediately at the time of harvest due to ischemia injury. Consequently increased organ viability during cold temperature storage and transport may be possible by flushing harvested organs with IL-1βTT biologics as well as adding them to preservation medium. Likewise IL-1βTT biologics administered to transplant recipients may improve allograft tolerance for reasons that have been described. Based on the aforementioned discussions it would seem reasonable to consider IL-1βTT in other pathobiological situations in which arterial perfusion is compromised and then reperfused by intervention, such as in replants, compromised blood supply from vascular injuries, compartment compression and for thrombo-embolic syndromes.

DETAILED DESCRIPTION OF THE INVENTION

Harvested organs exhibit classic IRI caused by systemic hypoxia from loss of arterial supply. There is concomitant breakdown of cells, nucleotides, freeing of ATP, intracellular hypokalemia, buildup of urates and calcium pyrophosphates which crystallize at lower pH. FIG. 1 illustrates an arterial blood vessel that is compromised either by partial or complete occlusion or by ablation as when an organ is harvested. The effect are hypoxia or anoxia contiguous to cells and tissue, and anaerobic acidosis as shown by a decrease in tissue pH. Next to the blood vessel is an enlarged tissue cell. All of the aforementioned biochemical effects are referred to as DAMPs (1). An enlarged cell (2) is shown with a cell membrane (3), nucleus (4), cytoplasm (5) which contains the aggregated NALP-3 inflammasome (6). PAMPs (7) are shown engulfed into cytoplasm (5). The DAMPs (1), such as crystallized urates or free ATP are detected by the cell membrane (3) and/or by being partially engulfed into the cytoplasm (5) and their presence in turn stimulate the NALP-3 inflammasome (6). IL-1β (8) is stored in the cytoplasm (5) as pro-IL-1β and stimulation of the NALP-3 inflammasome (6) by DAMPs (1) and PAMPs (7), cause the pro-IL-1β to be catalyzed to IL-1β (8), allowing it to be secreted into extracellular fluids. The secreted IL-1β (8) in turn causes attraction of neutrophils via a cascade of previously described immunologic events such as by attracting chemokines and by increased vascular adhesion molecule activation which in turn cause neutrophils to adhere to the intima of blood vessels followed by platelets and red cells accumulation, all leading to subsequent ischemia, The buildup of neutrophils causes activation of many other inflammatory events such as tissue damage by release of neutrophil proteases which damage cell and tissue integrity and by adhesion of neutrophils to blood vessel intima leading to more ischemia and hypoxia. This illustration does not demonstrate the worst case scenario, namely complete termination in arterial perfusion, such as during harvesting of organs for transplantation. There is evidence in this scenario, that harvested organs can exhibit an inflammatory cytokine burst immediately at the time of harvest due to ablation of arterial perfusion. This concept can explain why some harvested organs, such as kidneys, can begin to demonstrate signs of inflammation while they are being incubated up to 24 hours in cold fluids, and in turn explain to some degree why they are subsequently rejected following transplantation.

PAMPs (7) with DAMPs (1) or PAMPs (7) or DAMPs (1) individually can stimulate innate immune receptors such as the NALP-3 Inflammasome (6) and even some toll-like receptors to secrete IL-1β (8). Moreover the co-stimulation of the NALP3-inflammasome (6) by DAMPs (1) and PAMPs (7) together can cause synergistic IL-1β secretion, leading to greater inflammation.

These aforementioned observations provide a plausible explanation for the occurrence of neutrophilic inflammation in transplantation that is not likely caused by PAMPs, and provides a mechanism that is operable in understanding some of the pathobiology involving harvested organs and allograft rejection.

The following is presented as evidence:

1) There is evidence for the occurrence of metabolic acidosis in IR disorders caused by a combination of hypoxic induced anaerobic metabolism, lactic acidosis, ATP hydrolysis and carbon dioxide retention. Similar observations of tissue acidosis are likely to affect transplanted organs especially if they are harvested and preserved in cold ischemic-inducing solutions for long periods of time, such as up to 24 hours for some harvested kidneys. Acidosis can encourage development of DAMPs formation, such as crystallized uric acid/urates, as the solubility of urates is 1 to 4 mg/dl in a pH range of 3 to 6 versus 15 mg/dl or higher in pH>7.0. Similarly calcium phosphate/pyrophosphates can crystallize in acidic conditions and observers have noted their deposition in mitochondria of IR models. Moreover urates also crystallize optimally in cold temperatures with solubility of 4.5 mg/dl at 30° C. compared to 7.0 mg/dl at 37° C. Hence both tissue acidosis and hypothermia during transplantation procedures are ideal conditions for urate/calcium PP crystallization along with formation of other previously mentioned DAMPs from effects of acidosis, all of which are capable of stimulating IL-1β secretion from the NALP-3 inflammasome;

2) Elevated uric acid has been observed in recipients of cardiac, renal and hepatic transplantation. Numerous investigators have noted an unexplained association of hyperuricemia with increased risk of renal, cardiac and hepatic allograft rejection. The posited hypothesis may provide one explanation for organ rejection and dysfunction in association with elevations of this biomarker;

(3) Secretion of IL-1β in IR models is well established and similar observations have been noted in transplantation studies. Most of the evidence for IL-1β mediation of inflammation in transplantation is derived from studies with IL-1β TT comprising IL-1β receptor antagonists. Harada et al demonstrated that gene transfection of IL-1β receptor antagonist into rats subjected to liver IRI stress led to concomitant reduction in liver damage and increased survival rates in rats with gene transfection versus controls. Using cultures of kidney tissue obtained from human subjects with renal graft tolerance, De Oliveira et al demonstrated that an allograft tolerance factor was identifiable with the natural IL-1β receptor antagonist, further supporting the role of IL-1β as an important cytokine capable of contributing to allograft rejection. In pancreatic islet animal models, IL-1β receptor antagonist was shown to abrogate necrosis and enhance islet engraftment. A similar observation with transfected IL-1β receptor antagonist was observed protecting rodent myocardium from IR injury, and in an ex-vivo human atrial myocardial ischemia study with increased secretion of IL-1β, addition of IL-1β receptor antagonist improved myocardial contractility. Finally, evaluation of gene polymorphism for IL-1β and its receptor suggest their levels can predict graft outcomes, as haplotypes with predictably low production of IL-1β receptor antagonist and high IL-1β secretion may be risk factors for renal graft rejection.

Several FDA approved IL-1β TT biologics are commercially available, such as an IL-1β receptor blocker (anakinra), IL-1β TRAP (rilanocept) and a monoclonal anti-IL-1β antibody canakinumab). The use of these biologics over a combined three to four year or more time span in CAPS and other IL-1β mediated disorders has been efficacious with excellent safety profiles, as there have been minimal or no reports of serious adverse events with these compounds. Other caspase-1 inhibitors not yet FDA approved may also interfere in IL-1β function by inhibiting IL-1β secretion. It is again noteworthy to emphasize that there have been no known human trials or treatments with any of these biologics to preserve harvested organs and for transplantation procedures. The reticence to use IL-1 TT in humans undergoing organ transplantation should be partially overcome by the concepts promulgated in this invention.

BIBLIOGRAPHY

1. Martinon F, Burns K, Tschopp J. The inflammasome: a molecular platform triggering activation of inflammatory caspases and processing of prol L-1beta. Mol Cell 2002; 10: 417-426.
2. Chen C J, Kono H, Golenbock D, Reed G., Akira S, Rock K. Identification of a key pathway required for the sterile inflammatory response triggered by dying cells, Nat. Med. 2007; 13: 851-856.
3. Duncan J A, D. T. Bergstralh, Wang Y, Willingham S B, Ye Z, Zimmermann A G, Ting J P., Cryopyrin/NALP3 binds ATP/dATP, is an ATPase and requires ATP binding to mediate inflammatory signaling, Proc. Natl. Acad. Sci. U.S.A. 2007; 104: 8041-8046.
4. Martinon F, Petrilli V, Mayor A, Tardival A, Tschopp J. Gout associated uric acid crystals activate the NALP3 inflammasome. Nature 2006; 440:237-241.
5. Pétrilli V, Papin S, Dostert C, Mayor A, Martinon F, Tschopp J., Activation of the NALP3 inflammasome is triggered by low intracellular potassium concentration, Cell Death Differ. 2007; 14: 1583-1589.
6. Weinberg J M. The cell biology of ischemic renal injury. Kidney Int 1991; 39: 476-500.
7. Land W. Allograft injury mediated by reactive oxygen species from conserved proteins of *Drosophila* to acute and chronic rejection of human transplants. Part III: Interaction of oxidative stress-induced heat shock proteins with toll-like receptor-bearing cells of innate immunity and its consequences for the development of acute and chronic allograft rejection. Transplant Rev 2002; 17: 67-86.
8. Hoffman H M, Wright F M, Broide D H, Wanderer A A, Kolodner R D. Identification of a locus on chromosome 1q44 for familial cold urticaria. Am J Hum Genet 2000; 66:1693-98.
9. Martinon F, Burns K, Tschopp J. The inflammasome: a molecular platform triggering activation of inflammatory caspases and processing of prol L-1beta. Mol Cell 2002; 10: 417-426.
10. Hawkins P N, Lachmann H J, McDermott M F. Interleukin-1 receptor antagonist in the Muckle Wells syndrome. N Eng J Med 2003; 348: 2583-2584.
11. Hoffman H M, Rosengren S, Boyle D L., Cho J Y, Nayar J, Mueller J L, Anderson J P, Wanderer A A. Prevention of cold associated acute inflammation in familial cold Autoinflammatory syndrome by interleukin-1 receptor antagonist. Lancet 2004; 364: 1779-1785.
12. Aksentijevich I, Masters S L, Ferguson P J, Dancey P, Frenkel J, van Royen-Kerkhoff et al. An autoinflammatory disease with deficiency of the interleukin-1 receptor antagonist. N Eng J Med 2009; 360: 2426-2437.
13. Touzani O, Boutin H, Chuquet J, Rothwell N. Potential mechanisms of interleukin-1 involvement in cerebral ischemia. J. Neuroimmunol 1999; 100: 203-215.
14. Furuichi K, Wada T, Iwata Y, Kokubo S, Hara A, Yamahana J, et al., Interleukin-1-dependent sequential chemokine expression and inflammatory cell infiltration in IR injury. Crit. Care Med 2006; 34: 2447-2455.
15. Pomerantz B J, Reznikov L L, Harken A H, Dinarello C A. Inhibition of caspase-1 reduces human myocardial ischemia dysfunction via inhibition of IL-1β and IL-1. Proc Natl Acad Sci USA. 2001; 98: 2871-28.
16. Giamarellos-Bourboulis E J, Mouktaroudi M, Bodar E, van der Ven, J, Kullberg B-J, Netea M G, et al. Crystals of monosodium urate monohydrate enhance LPS-induced release of IL-1 by mononuclear cells through a caspase-1 mediated process. Ann Rheum Dis 2009; 68:273-278.
17. Boutilier R G. Mechanisms of cell survival in hypoxia and hypothermia. J Exp Biol 2001; 204: 3171-3181.
18. Vannucci R C, Vannucci S J. Perinatal hypoxic-ischemic brain damage: evolution of an animal model. Dev Neurosci 2005; 27: 81-86.
19. Weinberg J M. The cell biology of ischemic renal injury. Kidney Int 1991; 39:476-500.
20. Salahydeen A K. Cold ischemic injury of transplanted kidneys: new insights from experimental studies. Am J Physiol Renal Physiol 2004; 287: F181-F187.
21. Jennings R B, Sommers H M, Smyth G A, Flack H A, Linn H. Myocardial necrosis induced by temporary occlusion of a coronary artery in the dog. Arch Pathol 1960; 70: 68-78.
22. Harambat J, Dubourg L, Ranchin B, Hadj-Aissa A, Fargue S, Rivet C, Boillot O, Lachaux A, Cochat P. Hyperuricemia after liver transplantation in children. Pediatr Transplant 2008; 12: 847-853.
23. Kittleson M M, Bead V, Fradley M, St John M E, Champion H C, Kasper E K, Russell S D, Wittstein I S, Hare J M. Elevated uric acid levels predict allograft vasculopathy in cardiac transplant recipients. J Heart Lung Transplant 2007; 26: 498-503.
24. Bandukwala F, Huang M, Zaltzman J S, Nash M M, Prasad G V. Association of uric acid with inflammation, progressive renal allograft dysfunction and post-transplant cardiovascular risk. Am J Cardiol 2009; 103:867-871.
25. Harada H, Wakabayashi G, Takayanagi A, Shimazu M, Matsumoto K, Obara H, Shimizu N, Kitajima M. Transfer of the IL-1 receptor antagonist gene into rat liver abrogates hepatic IR injury. Transplantation 2002; 74: 1434-1441.

26. de Oliveira J G, Xavier P, Ramos J, Sampaio S, Magalhaes M, Mendes A, Pestana M. Cultures of kidney transplant fine-needle aspiration samples from rejection-free patients produces a specific antidonor response suppressive factor. Nephron 2002; 91: 637-645.
27. Schwarznau A, Hanson M S, Sperger J M, Schram B R, Danobeitia J S, Greenwood K K, Vijayan A, Fernandez L A. IL-1β receptor blockade protects islets against pro-inflammatory cytokine induced necrosis and apoptosis. J Cell Physiol 2009; 220: 341-437.
28. Manchanda P K, Bid H K, Kumar A, Mittal R D. Genetic association of interleukin-1 beta receptor antagonist (IL-1 Ra) gene polymorphism with allograft function in renal transplant patients. Transpl Immunol 2006; 15: 289-296.
29. Wanderer A A. Rationale and Timeliness for IL-1β Targeted Therapy to Reduce Allogeneic Organ Injury at Procurement and to Diminish Risk of Rejection after Transplantation. Clinical Transplantation. Jun. 1, 2010.

I claim:

1. A method to improve the viability of a harvested allograft transplant tissue or organ, said harvested allograft tissue or organ having inflammation from compromised arterial perfusion and/or exposure to cold temperature, comprising:
    harvesting said allograft tissue or organ; and
    contacting said harvested allograft tissue or organ directly with a cold temperature storage medium containing an IL-1β targeted therapeutic agent selected from the group consisting of an IL-1β receptor antagonist, an IL-1 TRAP, and an IL-1β monoclonal antibody;
    wherein said IL-1β targeted therapeutic agent neutralizes IL-1β derived from pro-IL-1β released from said harvested allograft tissue or organ and reduces said inflammation in said harvested allograft tissue or organ associated with compromised arterial perfusion and/or exposure to cold temperature,
    wherein said harvested allograft tissue or organ is flushed with said cold temperature storage medium containing an IL-1β targeted therapeutic agent immediately after time of harvest.

2. The method of claim 1, wherein said IL-1β targeted therapeutic agent is a biologic or chemical agent that causes a decrease in biological function of IL-1β.

3. The method of claim 1, wherein said inflammation is neutrophilic induced inflammation.

4. The method of claim 1, wherein said IL-1β targeted therapeutic agent is an IL-1β receptor antagonist.

5. The method of claim 1, wherein said IL-1β targeted therapeutic agent is an IL-1 TRAP.

6. The method of claim 1, wherein said IL-1β targeted therapeutic agent is an IL-1β monoclonal antibody.

7. The method of claim 1, 4, 5, or 6, wherein said harvested allograft tissue or organ comprises cardiac tissue.

8. The method of claim 1, 4, 5, or 6, wherein said harvested allograft tissue or organ comprises renal tissue.

9. The method of claim 1, 4, 5, or 6, wherein said harvested allograft tissue or organ comprises hepatic tissue.

10. The method of claim 1, 4, 5, or 6, wherein said harvested allograft tissue or organ comprises pancreatic islet tissue.

* * * * *